(12) United States Patent
Wong et al.

(10) Patent No.: US 11,096,793 B2
(45) Date of Patent: Aug. 24, 2021

(54) CALCANEAL PROSTHESIS

(71) Applicant: Wright Medical Technology, Inc., Memphis, TN (US)

(72) Inventors: Kian-Ming Wong, Lakeland, TN (US); Chris Robinson, Hernando, MS (US)

(73) Assignee: WRIGHT MEDICAL TECHNOLOGY, INC., Memphis, TN (US)

( * ) Notice: Subject to any disclaimer, the term of this patent is extended or adjusted under 35 U.S.C. 154(b) by 0 days.

(21) Appl. No.: 16/495,925

(22) PCT Filed: Jun. 13, 2017

(86) PCT No.: PCT/US2017/037209
§ 371 (c)(1),
(2) Date: Sep. 20, 2019

(87) PCT Pub. No.: WO2018/231202
PCT Pub. Date: Dec. 20, 2018

(65) Prior Publication Data
US 2020/0129302 A1    Apr. 30, 2020

(51) Int. Cl.
*A61F 2/42* (2006.01)
*A61B 17/72* (2006.01)
*A61F 2/30* (2006.01)

(52) U.S. Cl.
CPC ............ *A61F 2/4202* (2013.01); *A61B 17/72* (2013.01); *A61F 2/30942* (2013.01);
(Continued)

(58) Field of Classification Search
CPC .............. A61B 17/72; A61B 2017/564; A61B 17/8061; A61B 2017/681; A61B 17/1725;
(Continued)

(56) References Cited

U.S. PATENT DOCUMENTS 6,572,620 B1   6/2003  Schon et al.
6,579,293 B1   6/2003  Chandran
(Continued)

FOREIGN PATENT DOCUMENTS

CN    106691635 A     5/2017
FR      2895664 A1    7/2007
(Continued)

OTHER PUBLICATIONS

International Search Report and Written Opinion issued in connection with corresponding International Patent Application No. PCT/US2017/037209, 9 pages, dated Feb. 22, 2018.
(Continued)

*Primary Examiner* — Ann Schillinger
(74) *Attorney, Agent, or Firm* — Duane Morris LLP

(57) ABSTRACT

A calcaneal prosthesis system includes a body having a dorsal surface, a plantar surface, an anterior surface, and a posterior end. The posterior end has a tuberosity. The anterior surface has at least a concavity or convexity shaped for receiving a cuboid bone or mid-foot bone. The dorsal surface includes a convex or concave surface for engaging a talus bone or distal tibia. The body has a first previously formed surface defining a hole extending through the body for receiving an intramedullary (IM) nail. The hole extends from the plantar surface of the body to the dorsal surface.

16 Claims, 17 Drawing Sheets

(52) U.S. Cl.
CPC .............. *A61F 2002/30878* (2013.01); *A61F 2002/30962* (2013.01); *A61F 2002/4217* (2013.01)

(58) Field of Classification Search
CPC ... A61B 17/1775; A61B 17/725; A61B 17/80; A61B 17/7241; A61B 17/7283; A61B 17/744; A61B 17/1728; A61B 17/7233; A61B 17/8057; A61B 17/164; A61F 2/4202; A61F 2/4606; A61F 2002/30622; A61F 2002/4207; A61F 2/28; A61F 2002/4217; A61F 2310/00359; A61F 2002/4212
See application file for complete search history.

(56) References Cited

U.S. PATENT DOCUMENTS

| | | | |
|---|---|---|---|
| 7,410,488 | B2 | 8/2008 | Janna et al. |
| 8,491,583 | B2 | 7/2013 | Gall et al. |
| 2003/0097131 | A1* | 5/2003 | Schon ................ A61B 17/72 606/62 |
| 2005/0125070 | A1* | 6/2005 | Reiley ................ A61F 2/4202 623/21.18 |
| 2013/0325006 | A1 | 12/2013 | Michelinie et al. |
| 2015/0045903 | A1 | 2/2015 | Neal et al. |
| 2016/0338842 | A1 | 11/2016 | Adams |

FOREIGN PATENT DOCUMENTS

| | | |
|---|---|---|
| RU | 2515391 C1 | 5/2014 |
| WO | 2006091460 A1 | 8/2006 |
| WO | 2013181358 A1 | 12/2013 |

OTHER PUBLICATIONS

Richter, M., et al., "Tibiotalocalcaneal Arthrodesis with a Triple-Bend Intramedullary Nail (A3)-2-year follow-up in 60 Patients," Foot and Ankle Surgery, 2016, vol. 22, Issue 2, pp. 131-138, See pp. 131-137.

Varma, et al., "Use of Poly Methyl Methacrylate as Prosthetic Replacement of Destroyed Foot Bones—Case Series", The Journal of Diabetic Foot Complications, 2012; vol. 4, Issue 3, No. 3, pp. 71-82.

Imanishi, et al., "Three-dimensional printed calcaneal prosthesis following total calcanectomy", Mar. 10, 2015, Int J Surg Case, Rep. 2015; 10:83-87.

Millsaps, Bridget Butler, "Another First in Korea: Young Man Receives 3D Printed Heel Bone, Avoids Amputation,", Jun. 18, 2016, 3D Print.com.

Chou, et al, "Osteosarcoma of the Calcaneus Treated with Prosthetic Replacement with Twelve Years of Followup: A Case Report", Foot & Ankle International, 2007.

Biomet Orthopedics, "Phoenix Ankle Arthrodesis Nail System," 2013.

Catanzariti, et al., "Intramedullary nail fixation for reconstruction of the hindfoot and ankle in charcot neuroarthropathy", 2009, Surgical reconstruction of the diabetic foot and ankle by Thomas Zgonis.

www.3ders.org, "Australian Doctors Use 3D Printer to Save 71-Year-old Cancer Suffer's Foot", 9 pages, Oct. 20, 2014, www.3ders.org/articles/20141020-australian-doctors-use-3d-printer-to-save-71-year.

First Examination Report issued in connection with corresponding Australian Patent Application No. 2017418982, dated Jan. 15, 2020, 3 pages.

First Office Action issued in connection with corresponding Canadian Patent Application No. 3,057,600, dated Nov. 9, 2020, 3 pages.

Extended European Search Report in connection with corresponding European Patent Application No. 179913516.5, dated Nov. 11, 2020, 7 pages.

* cited by examiner

CALCANEAL PROSTHESIS

CROSS REFERENCE TO RELATED APPLICATION

This is a National Stage Application, filed under 35 U.S.C. 371, of International Patent Application No. PCT/US2017/037209, filed on Jun. 13, 2017, contents of which is incorporated herein by reference in its entirety.

FIELD

This disclosure relates generally to medical devices and more specifically to a calcaneal prosthesis.

BACKGROUND

Arthrodesis refers to surgical fixation of a joint, ultimately resulting in bone fusion. An arthrodesis procedure induces ankylosis performed to relieve pain or provide support in a diseased or injured joint. Tibiotalocalcaneal or tibiocalcaneal arthrodesis ("TC") is a salvage procedure for the treatment of joint disease or pain and dysfunction due to arthritic ankle and subtalar joints, e.g., Charcot disease. In performing ankle and subtalar arthrodesis, the surgeon may wish to achieve anatomic alignment, pain relief, and a stable, plantigrade foot. Secure fixation while preserving the surrounding soft tissue can also contribute to a successful outcome.

Intramedullary (IM) nails (also referred to as "rods") have been used for tibiotalocalcaneal or tibiocalcaneal arthrodesis. The IM nail fixes the calcaneus, talus and tibia in alignment, for fusing these three bones together. The surgeon can lock the IM nail using bone screws connected to each end of the IM nail. The bone screws fix the position of the IM nail relative to the cortical bone.

SUMMARY

In some embodiments, a calcaneal prosthesis system comprises a body having a dorsal surface, a plantar surface, an anterior surface, and a posterior end. The posterior end has a tuberosity. The anterior surface has at least a concavity or convexity or flat surface shaped for receiving a cuboid bone. The dorsal surface includes a convex, concave, or flat surface for engaging a talus bone. The body has a first previously formed surface defining a hole extending therethrough for receiving an intramedullary (IM) nail. The hole extends from the plantar surface of the body to the dorsal surface.

In some embodiments, a calcaneal prosthesis comprises a single-piece body having a dorsal surface, an anterior surface, and a posterior end. The posterior end has a tuberosity. The anterior surface has a concavity shaped for receiving a cuboid bone or mid-foot bone(s). The dorsal surface includes a convex surface for engaging a talus bone or distal tibia. The unitary body has an integral intramedullary (IM) nail protruding from the dorsal surface.

In some embodiments, a method of making a calcaneal prosthesis includes: collecting image data defining a first three-dimensional (3D) model of a first calcaneus of a patient; forming a second 3D model of a second calcaneus by computing a mirror image of the first 3D model about a sagittal plane; adding to the second 3D model at least one surface defining a hole that extends through the second calcaneus, the hole sized and shaped to receive an intramedullary nail; and fabricating the calcaneal prosthesis according to the second 3D model, using an additive manufacturing process.

DETAILED DESCRIPTION

Figure 1:
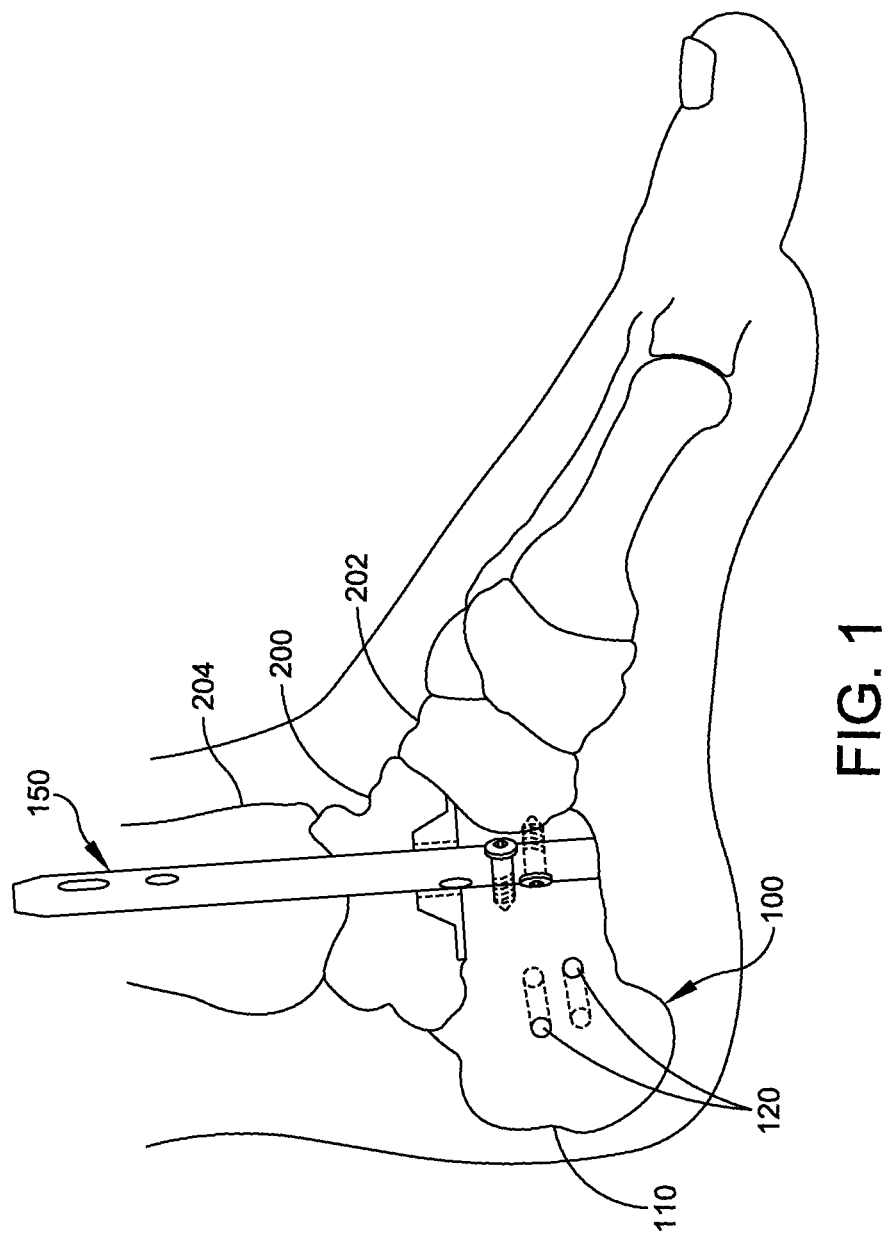
FIG. 1 is a medial view of a left foot with a calcaneal prosthesis system.

This description of the exemplary embodiments is intended to be read in connection with the accompanying drawings, which are to be considered part of the entire written description. In the description, relative terms such as "lower," "upper," "horizontal," "vertical,", "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

This disclosure describes a calcaneal prosthesis having one or more pre-drilled holes configured for receiving at least an intramedullary (IM) nail. This disclosure also describes a single-piece calcaneal prosthesis having an integrally formed IM nail extending from a dorsal surface of the calcaneal prosthesis. In cases where the patient's calcaneus has degraded, the calcaneal prosthesis provides a strong base for retaining the IM nail in position for fusing the calcaneal prosthesis, talus and tibia. Further, calcaneal prosthesis systems are provided.

FIGS. 1-6 show a first embodiment of a calcaneal prosthesis 100. FIG. 1 is a schematic diagram of a left foot having a calcaneal prosthesis 100 and intramedullary nail 150 implanted therein. The calcaneal prosthesis 100 is configured to approximate the shape and function of a natural calcaneus, including the calcaneal tuberosity 119. In some embodiments, the prosthesis 100 has a dorsal surface adapted to abut a resected talus 200 or resected tibia. In some embodiments, the prosthesis 100 has an anterior surface adapted to abut a resected cuboid 202 and/or mid-foot bones. In the configuration shown in FIG. 1, the IM nail 150 is inserted through the calcaneal prosthesis 100, the talus 200 and the tibia 204, for fusing the calcaneal prosthesis 100, the talus 200 and the tibia 204 together. In other embodiments, for a patient having a severely degraded talus, the prosthesis 100 can have an extended plantar-dorsal height, and the IM nail 150 is extended through the calcaneal prosthesis 100, and directly into the tibia 204.

Figure 2:
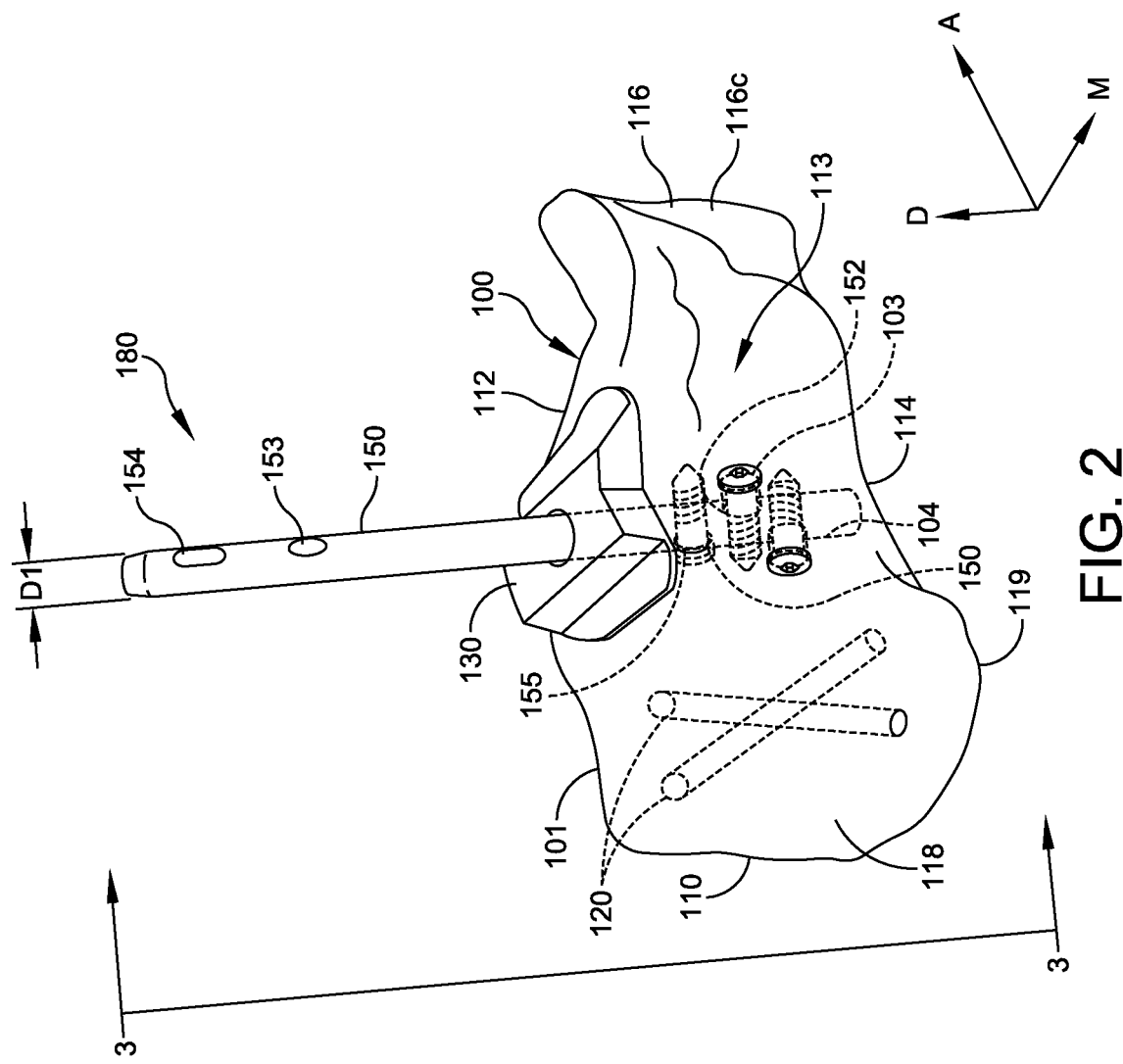
FIG. 2 is a medial isometric view of the calcaneal prosthesis system of FIG. 1.
Figure 3:
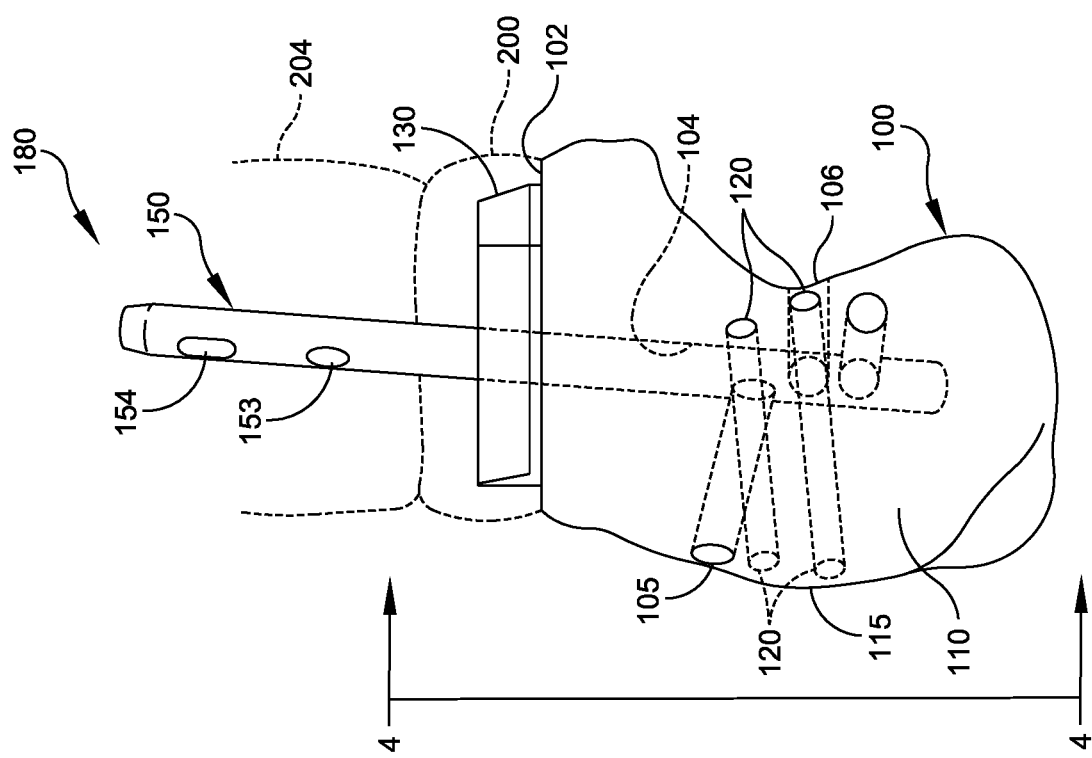
FIG. 3 is a posterior view of the calcaneal prosthesis system of FIG. 1.
Figure 4:
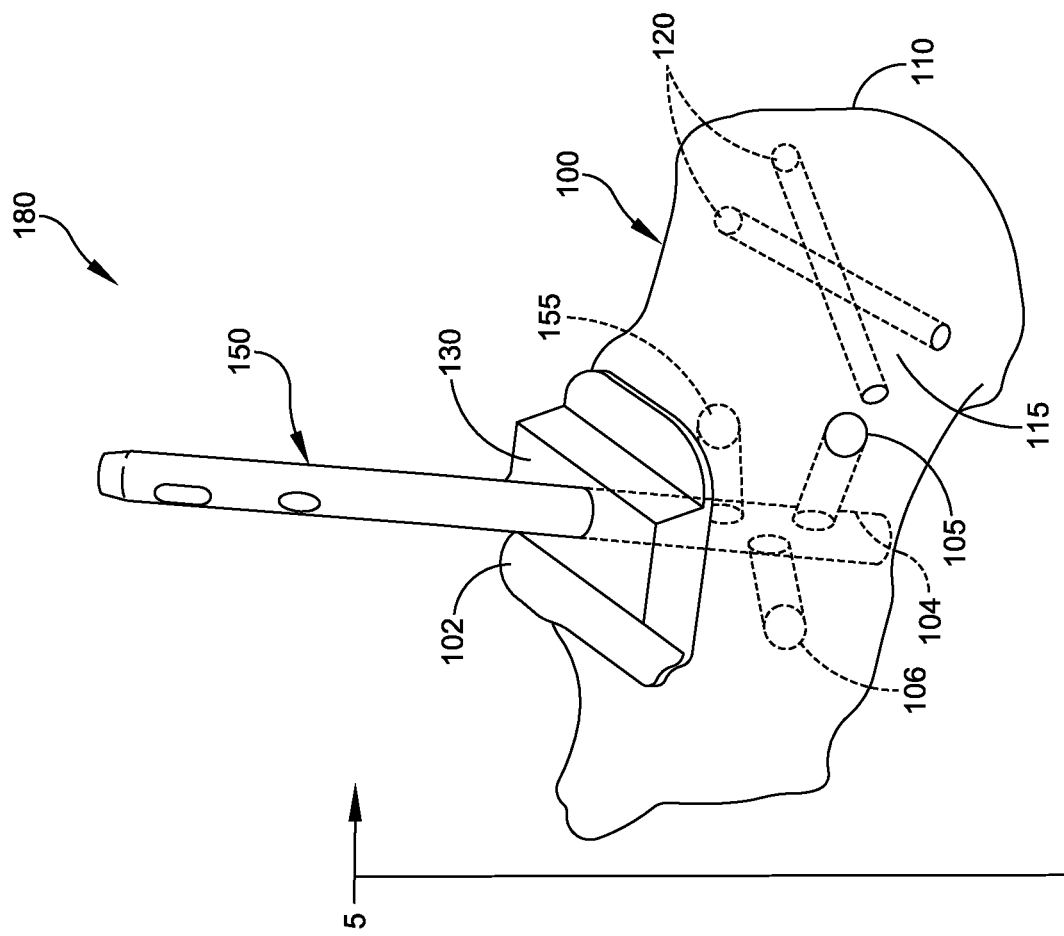
FIG. 4 is a lateral view of the calcaneal prosthesis system of FIG. 1.
Figure 5:
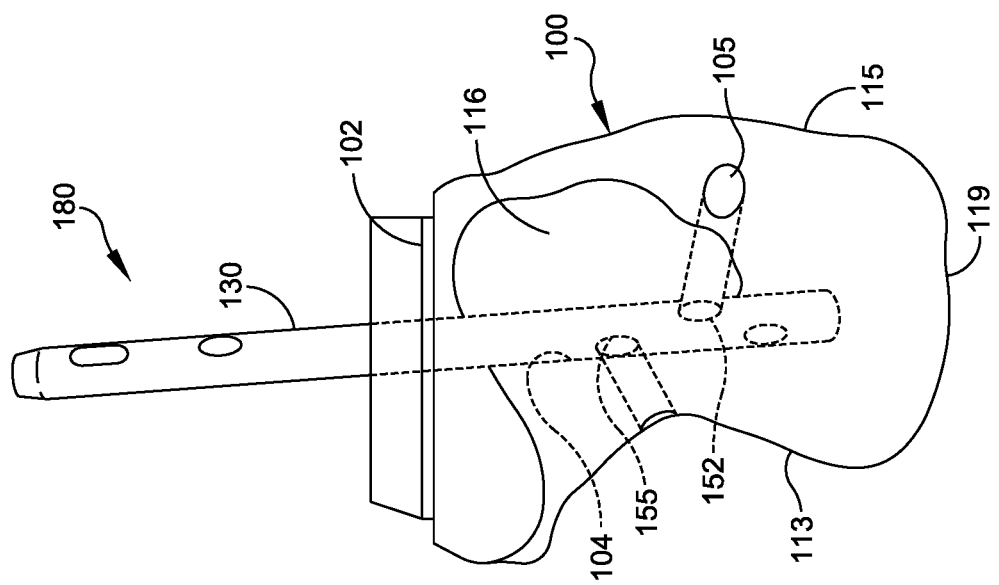
FIG. 5 is an anterior view of the calcaneal prosthesis system of FIG. 1.
Figure 6:
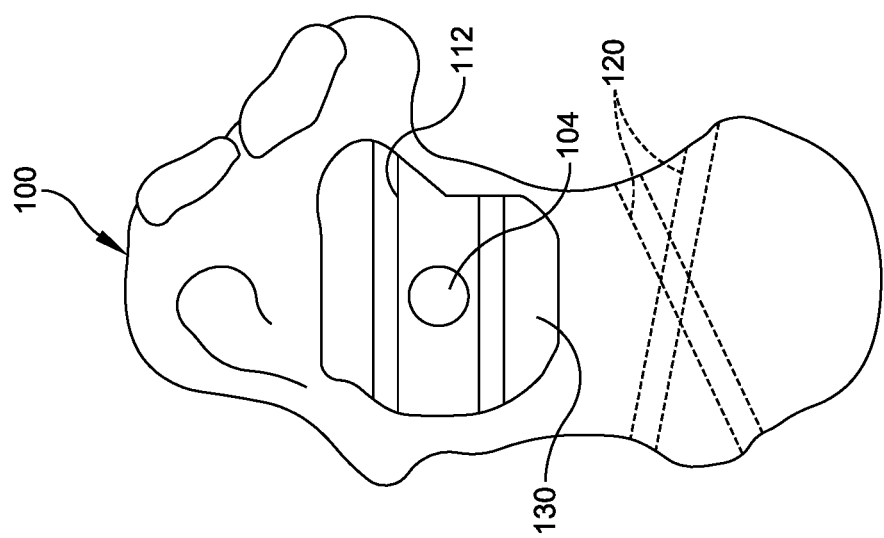
FIG. 6 is a superior view of the calcaneal prosthesis system of FIG. 1.

In some embodiments, a calcaneal prosthesis system 180 may be employed including the calcaneal prosthesis 100. In more detail, as shown in FIGS. 2-6, the calcaneal prosthesis system 180 comprises a body 110 having a dorsal surface 112, a plantar surface 114, a medial surface 113, a lateral surface 115, an anterior surface 116, and a posterior end 118. The anterior (A), medial (M) and dorsal (D) directions are shown in FIG. 2. The posterior end 118 has a tuberosity 119. The tuberosity 119 extends in an oblique direction relative to an anterior-posterior (A) direction of the body.

In some embodiments, the anterior surface 116 has a concavity, convexity or flat surface shaped for receiving the cuboid bone 202 or mid-foot bone(s). For example, the anterior surface 116 can include a concavity 116c as shown in FIG. 2. The concavity is shaped as an articulating surface for articulating motion with respect to the cuboid 202—or mid-foot bone(s) in a case where the surgeon makes a biplanar wedge cut to the mid-foot. In other embodiments described below with reference to FIGS. 14 and 15, the anterior surface can include a trapezoid-shaped projection or a trapezoid-shaped recess, respectively, for abutting a resected cuboid (not shown) and/or mid-foot bone(s), not shown.

In the example of FIGS. 2-6, the dorsal surface 112 includes a convex surface for engaging a talus bone 200 and/or tibia. For example, because the exemplary prosthesis 100 is intended for use in a fusion surgery, the dorsal surface 112 can include a trapezoid-shaped convexity 130 as shown in FIG. 2, adapted to be received by a recess in a resected talus (not shown). The exemplary trapezoid-shaped convexity 130 has the general form of a truncated pyramid, with trapezoidal surfaces on the medial, lateral, anterior and posterior sides, to facilitate an approach from any direction the surgeon may choose. In other embodiments described below with reference to FIG. 13, the dorsal surface can include a trapezoid-shaped recess, for abutting a corresponding projection of a resected talus (not shown). In other embodiments, a concave or flat surface can be substituted for the convex surface on the dorsal surface 112 of the body. Further, convex surfaces can be curved or can comprise combinations of flat and/or curved surfaces that form a protuberance; concave surfaces can be curved or can comprise combinations of flat and/or curved surfaces that form a recess.

The body 110 has a pre-formed surface defining a hole 104 therethrough for receiving an IM nail 150. In particular, the previously formed hole 104 may be pre-drilled, or pre-made by forging, casting and/or machining. In other embodiments, the surfaces defining the holes 104 are formed as part of an additive manufacturing (AM) process, such as 3D printing or direct metal laser sintering (DMLS) as discussed below. If an AM process is used, the prosthesis 100 is formed as a plurality of stacked monolayers, and holes are formed by voids at selected locations within the monolayers. The surfaces defining pre-formed hole 104 may be pre-planned using patient specific planning. In some embodiments, the detailed shape of the non-degraded calcaneus is determined (e.g., by CT scan), a mirror image of the shape is formed about the mid-sagittal plane, and an AM process is used to construct the prosthesis according to the mirror image. A patient-specific manufacturing method for forming the prosthesis 100 is described below in the discussion of FIG. 17.

In other embodiments, one or more "generic" calcaneus implants can be provided with multiple sizes. For example, after removing the degraded calcaneal tissue, the surgeon can insert one or more calcaneal prosthesis trials (not shown) for purpose of finding the standard size calcaneal prosthesis that most closely fits the foot anatomy of the patient. The surgeon then implants a calcaneal prosthesis having a size corresponding to the most closely-fitting calcaneal prosthesis trial. If the trial method is used, the surgeon can fit the calcaneal prosthesis without scanning the healthy calcaneus of the opposite foot.

The hole 104 extends from the plantar surface 114 of the body 110 to the dorsal surface 112 of the body 110. In the case where the prosthesis is molded or formed by additive manufacturing (e.g., 3D printing or direct metal laser sintering), the surface defining hole 104 is formed at the same time the prosthesis is formed. In the case where the prosthesis 100 is formed by machining, the surface defining hole 104 may be formed at any time point before, during or after the machining process. Forming the surface defining hole 104 at the beginning of machining provides more options for stabilizing the piece of material from which the prosthesis is formed during the remainder of the machining. Forming the surface defining hole 104 during fabrication of the calcaneal prosthesis 100 reduces the length of the surgery preparation and avoids the difficulty of the surgeon drilling an aligned hole in the irregularly shaped calcaneal prosthesis 100.

A plurality of fastener openings (e.g., screw-receiving openings) penetrate the body 110 from the medial surface 113, lateral surface 115, anterior surface 116 and/or posterior end 118. The fastener openings 105, 106 extend from the external surface of the calcaneal prosthesis 100 to the hole 104. In some embodiments, the IM nail 150 has a set screw that can be advanced within the nail to compress the joint. In some embodiments, the surgeon can implant bone screws into the calcaneal prosthesis 100 and into aligned screw-receiving holes in the IM nail, to stabilize the IM nail and prevent it from loosening or moving. Prosthesis 100 can also have surfaces defining additional fixation holes from medial, lateral, or posterior side of the calcaneal to fuse calcaneal to cuboid and/or mid-foot bones. For example, FIGS. 2-6 show a fastener opening 106 on the medial surface 113 and a fastener opening 105 on the lateral surface 115. The at least one fastener opening can be oriented at an oblique angle relative to the hole. These are just exemplary locations and orientations. The fastener opening can be provided at different locations (not shown). The fastener openings 105, 106 can be oriented at a variety of different angles. Additional fastener openings can be included, and the number of fastener openings is not limited to two. For example, some embodiments also have surfaces defining additional fixation holes from medial, lateral, or posterior side of the calcaneal to fuse calcaneal to cuboid and/or mid-foot bones.

The body 110 can have one or more openings 120 for receiving k-wires for external fixation. The example in FIGS. 1-6 has two openings 120, but other embodiments can have any number of openings for external fixation. The openings 120 can extend part way into the body 110 or extend from one (e.g., lateral) side to the opposite (e.g., medial) side as shown. The k-wires can be attached to an external fixation device, such as a circular fixator or the like (not shown).

The calcaneal prosthesis system 180 further comprises an intramedullary (IM) nail 150 shaped to extend through the hole 104. The IM nail 150 has at least one aperture 151, 152 configured to receive at least one fastener (e.g., a bone screw, not shown) extending through the at least one fastener opening 105, 106 of the body 110.

The IM nail 150 comprises a material such as titanium, a titanium alloy (e.g., Ti 6Al-4V) or stainless steel, or cobalt chrome (CoCr).

The IM nail 150 has an elongated shape. In some embodiments, the IM nail has a first diameter D1 along its entire length, as shown in FIG. 2. In other embodiments (as discussed below with reference to FIG. 7, the IM nail has a stop to prevent the IM nail from moving toward the tibia 204 when pressure is applied to the foot.

The exemplary calcaneal prosthesis system 180 allows implantation of an IM nail, even in the case where the patient's calcaneus is deteriorated, such as in the case of Charcot disease. The surgeon can replace the calcaneus with the calcaneus prosthesis 100 and then insert the IM nail 150. The calcaneus prosthesis 100 provides a strong, aligned implant for securing the IM nail 150. The previously formed surface defining hole 104 and fastener openings 105, 106 avoid any need for the surgeon to drill through the calcaneus prosthesis 100 and avoid alignment errors due to incorrect drilling by the surgeon.

Although FIGS. 1-6 show a calcaneal prosthesis system 180 for a left foot, a calcaneal prosthesis for the right foot (not shown) can share the same design elements arranged as a mirror image of calcaneal prosthesis system 180 with respect to the mid-sagittal plane.

In some embodiments, a method for implanting the calcaneal prosthesis system 180 of FIGS. 1-6 comprises implanting a calcaneal prosthesis 100 through a medial incision, a lateral incision, an anterior incision, or a posterior incision in a foot. For example, a method of implanting the calcaneal prosthesis system 180 can include making an incision for inserting the calcaneal prosthesis 100 from a desired side (e.g., an anterior approach). Depending on the quality of the talar bone 200 and the configuration of the dorsal surface of the calcaneal prosthesis 100, the surgeon may resect the talus 200 to include a recess or a protuberance. The surgeon may place pins in the talus 200 and/or cuboid 202 for aligning the calcaneal prosthesis 100 during implantation.

The calcaneal prosthesis 100 is inserted into the wound site. The calcaneal prosthesis 100 has a pre-planned hole 104 therethrough. The hole 104 extends from a plantar surface 114 of the calcaneal prosthesis to a dorsal surface 112 of the calcaneal prosthesis 100. The surgeon drills to extend the hole for the IM nail 150 through the talus 200 and tibia 204 from a plantar approach. Then the IM nail 150 is inserted through a plantar incision in the foot and through the hole 104 of the calcaneal prosthesis 100, through the talus 200 and into the tibia 204. The surgeon inserts one or more bone screws through a fastener opening 105, 106 in a medial side 113, lateral side 115, anterior side 116, or posterior side 118 of the calcaneal prosthesis 100 and into a corresponding aperture in the IM nail 150. The fasteners (e.g., bone screws) are inserted through the calcaneal prosthesis 100 and into the apertures 151, 152, 155 of the IM nail 150 to lock the IM nail 150 in place. For example, the surgeon may insert three screws: a transverse calcaneal screw, a posterior calcaneal screw, and subtalar screw (if the patient's talus is intact). The surgeon also inserts one or more bone screws through the tibia 204 and into the IM nail 150. The calcaneal prosthesis system 180 can be advantageous if the surgeon wants to use an anterior, posterior, lateral or medial approach for inserting the calcaneal prosthesis 100.

Figure 7A:
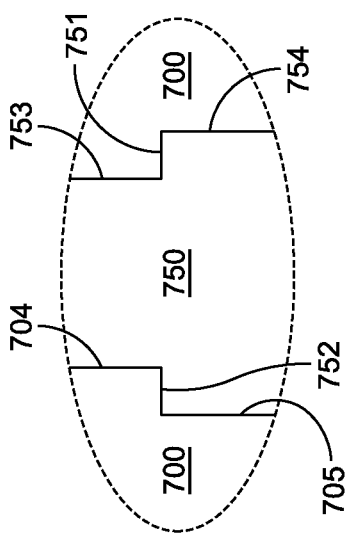
FIG. 7A is an enlarged detail of FIG. 7.
Figure 7:
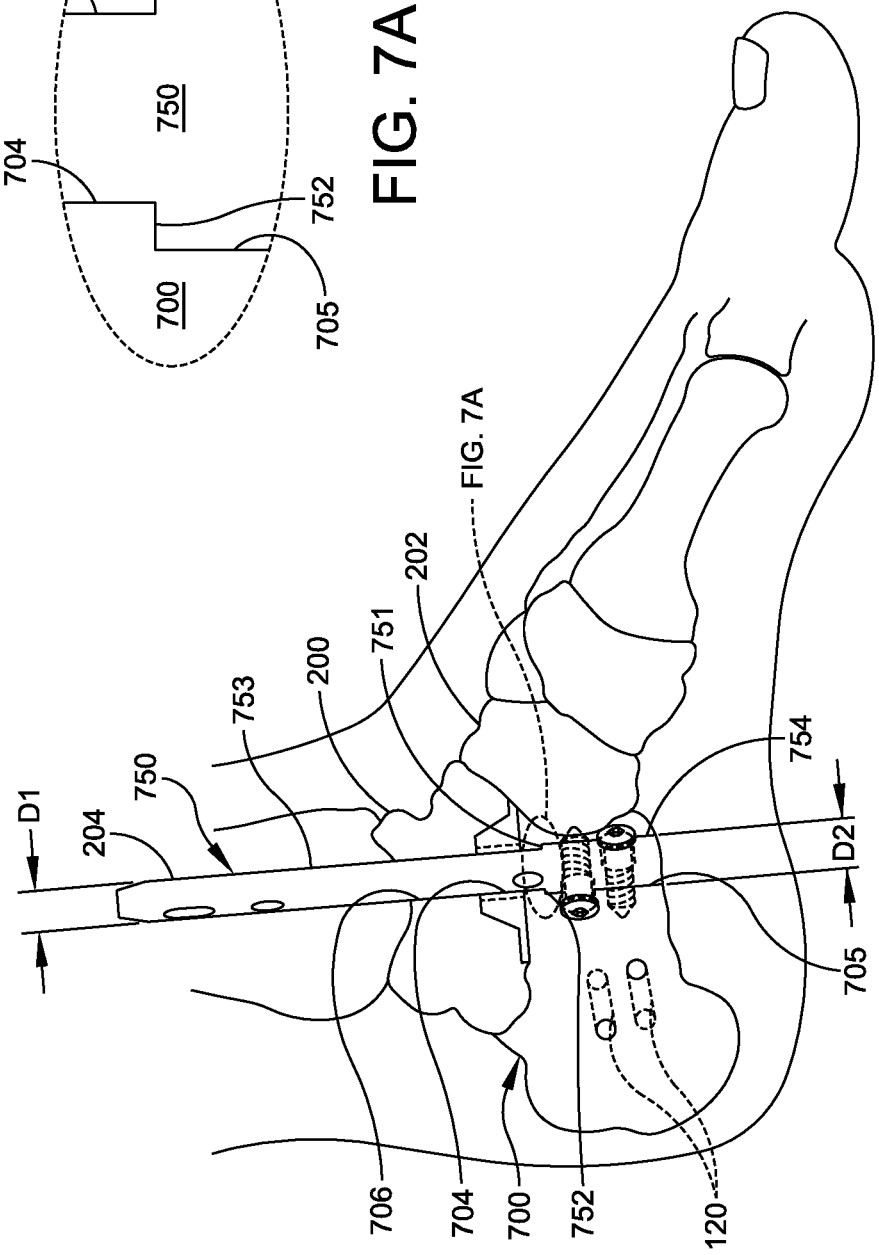
FIG. 7 is a medial view of a left foot with a variation of the calcaneal prosthesis system of FIG. 1.

FIG. 7 shows an embodiment of a calcaneal prosthesis system 780 in which the IM nail 750 has a shoulder 751, and the calcaneal prosthesis 700 has a corresponding stop 752 for limiting a depth of insertion of the IM nail 750. FIG. 7A is an enlarged detail of FIG. 7, showing the shoulder 751 of IM nail 750 abutting the stop 752 within the hole. In FIG. 7, the IM nail 750 has a first portion 753 (e.g., a dorsal portion) with a first diameter D1, and a second portion 754 (e.g., plantar portion) with a second diameter D2 different from the first diameter D1. The surface defining the hole in the body 700 has a first part 704 sized to receive the first portion 753 of the IM nail 750 and a second part 705 sized to receive the second portion 754 of the IM nail 750. The stop 752 is located at the interface between the first part 704 and the second part 705. When the IM nail 750 is inserted through the calcaneal prosthesis 700 and the talus 200, the shoulder 751 of the IM nail 750 abuts the stop 752 and prevents the IM nail 750 from traveling further into the tibia 204. The stop 752 can be formed by a counter bore 705 in the plantar surface of the calcaneal prosthesis 700. In some embodiments, as shown in FIG. 7 the stop 752 is located within the calcaneal prosthesis 700.

Although IM nail 750 has an increase in diameter from D1 to D2 where the first portion 753 meets the second portion 754, this is not a requirement. In other embodiments (not shown), the IM nail has a gradual taper from the first diameter D1 to the second diameter D2. The calcaneal prosthesis 700 can have a corresponding gradual taper from the first diameter D1 to the second diameter D2. The tapered portion (not shown) of the surface defining the hole in the calcaneal prosthesis can act as the stop.

In another embodiment (not shown), the second portion 754 of the IM nail 750 extends from the plantar surface of the calcaneal prosthesis to the dorsal surface of the calcaneal prosthesis. The surface defining hole 705 has the larger diameter D2 for the entire distance from the plantar surface of the calcaneal prosthesis 700 to the dorsal surface of the calcaneal prosthesis. The surface defining hole 706 in the talus 200 and tibia 204 has the smaller diameter D1, and the cortical bone of the talus 200 provides the stop 752.

The method for implanting the calcaneal prosthesis 700 is similar to the method described above for implanting the calcaneal prosthesis system 180 of FIG. 1 As noted above, the IM nail 750 has a first portion 753 with a first diameter D1, a second portion 754 with a second diameter D2 larger than the first diameter D1, and a shoulder 751 at an interface between the first portion 753 and the second portion 754. The surface defining hole in the calcaneal prosthesis 700 has a first part 704 sized to receive the first portion 753 of the IM nail 750 and a second part 705 sized to receive the second portion 754 of the IM nail 750. The step of inserting the IM nail 750 into the hole 704, 705 includes advancing the IM nail 750 until the shoulder 751 of the IM nail 750 abuts the stop 752 of the opening 705.

FIGS. 8-12 show an embodiment of a single-piece calcaneal prosthesis 800 for a left foot. Except where expressly indicated below, the shape of the prosthesis 800 can be the same as the shape of the prosthesis 100 of FIGS. 1-6.

Figure 8:
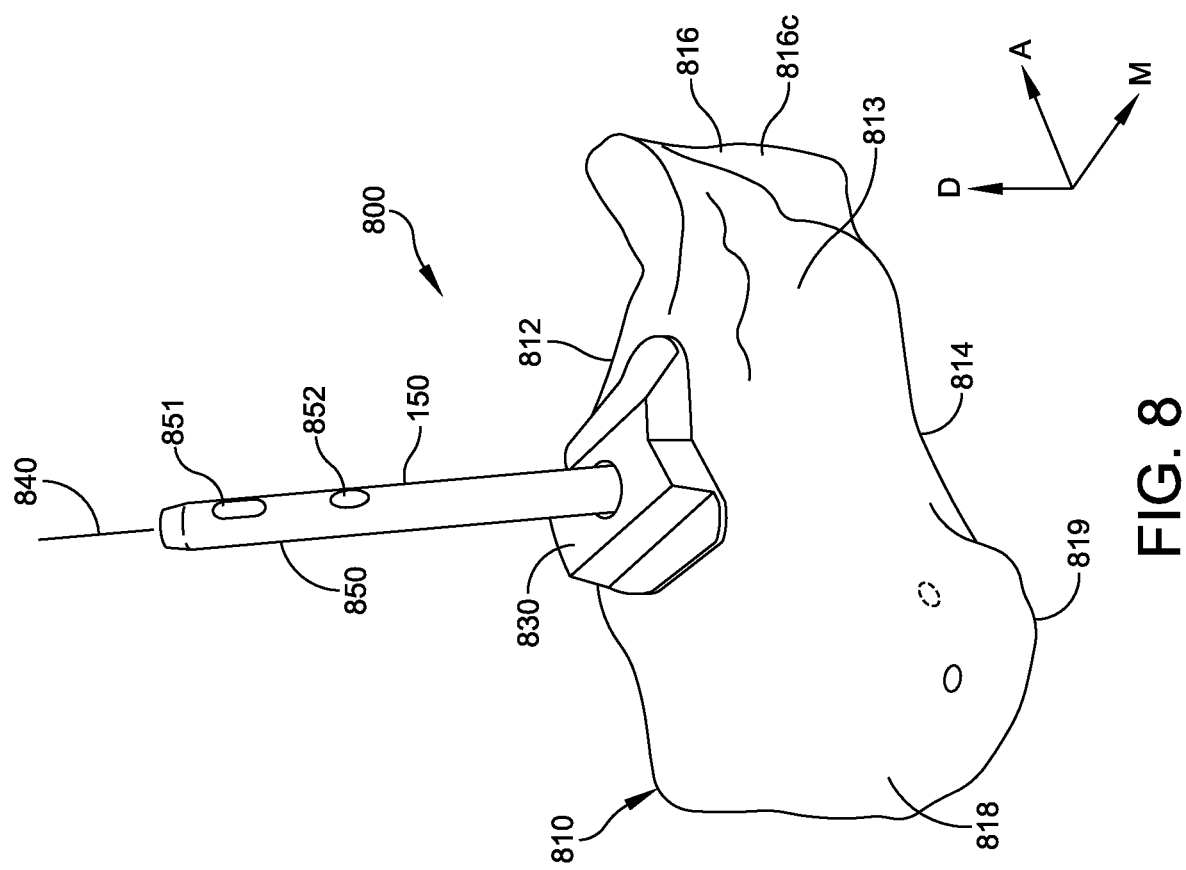
FIG. 8 is a medial isometric view of a single-piece calcaneal prosthesis system.
Figure 9:
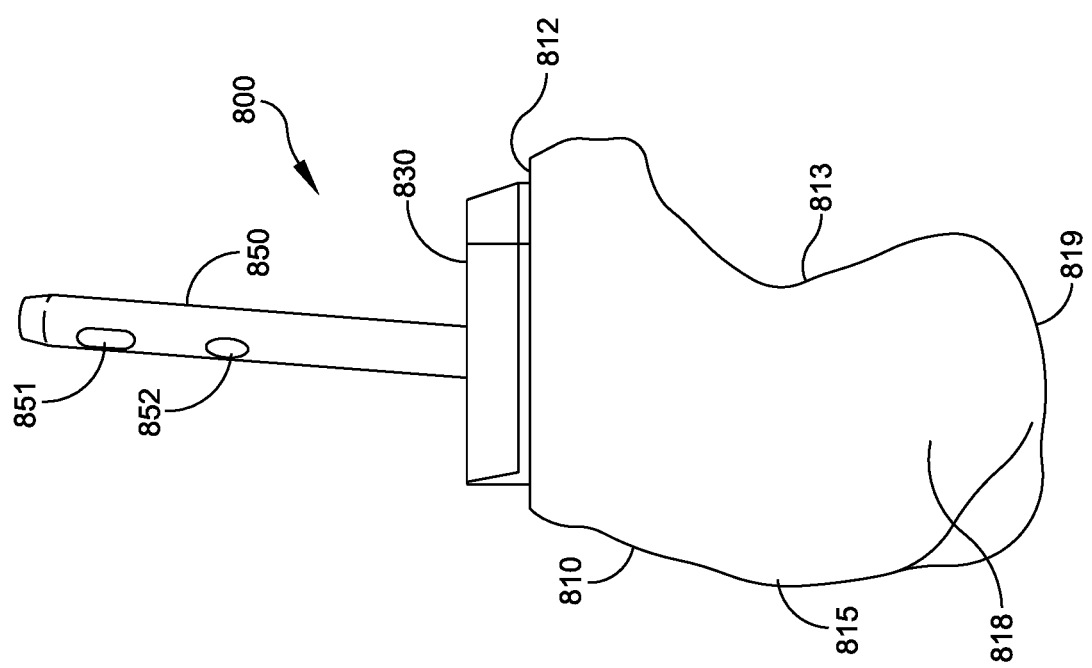
FIG. 9 is a posterior view of the calcaneal prosthesis system of FIG. 8.
Figure 10:
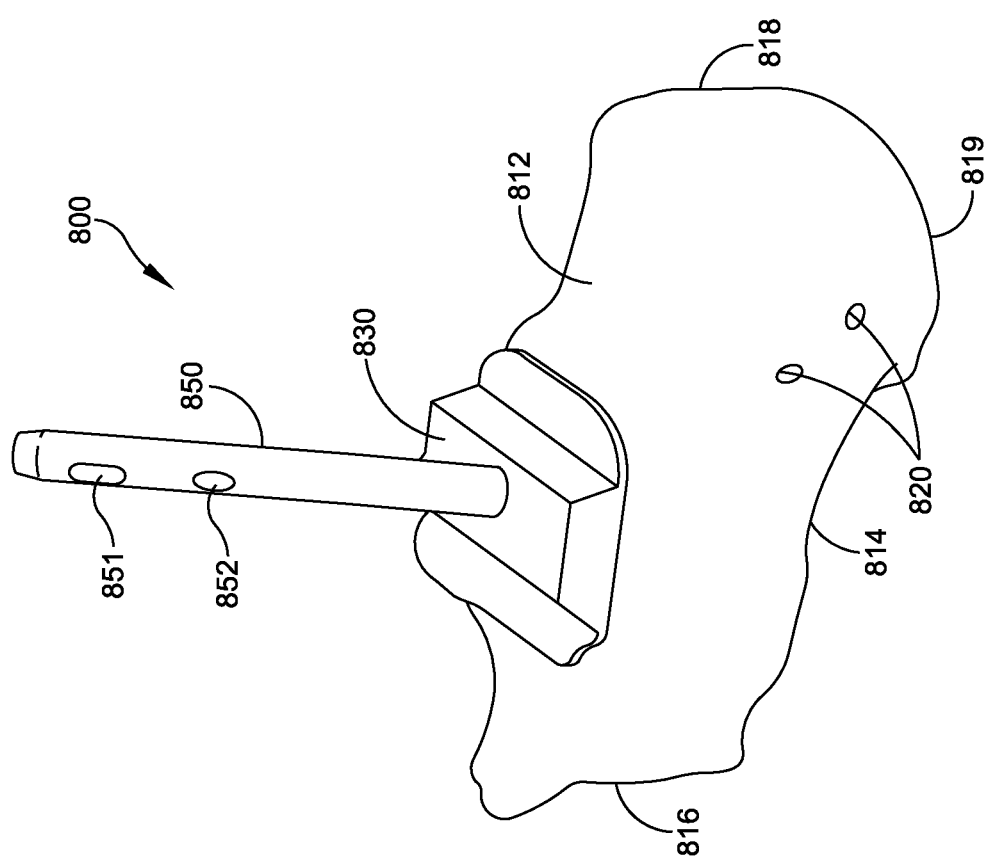
FIG. 10 is a lateral view of the calcaneal prosthesis system of FIG. 8.
Figure 11:
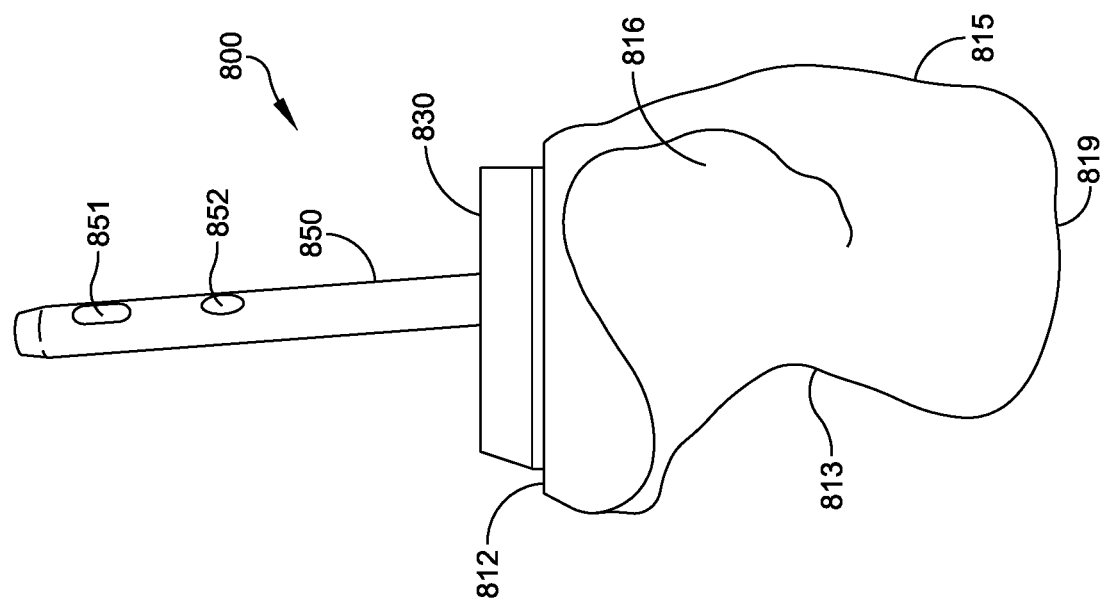
FIG. 11 is an anterior view of the calcaneal prosthesis system of FIG. 8.
Figure 12:
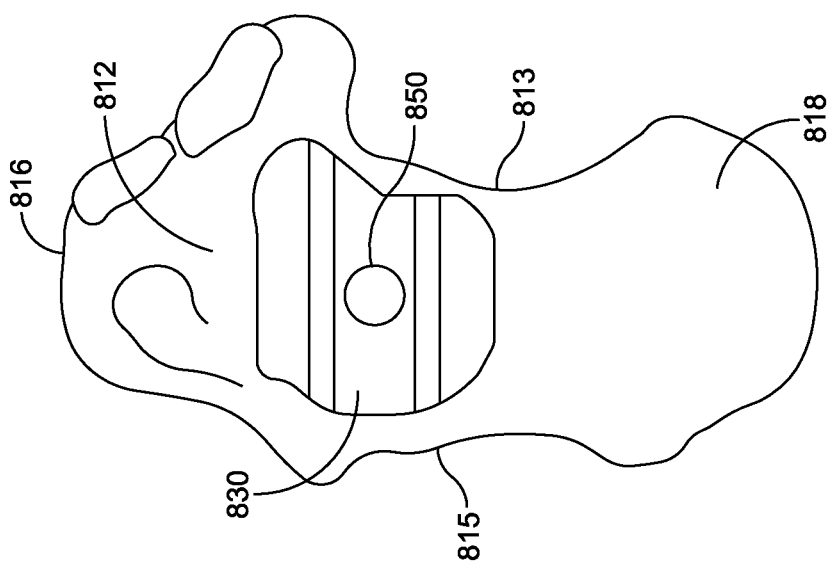
FIG. 12 is a superior view of the calcaneal prosthesis system of FIG. 8.

FIG. 8 is a schematic diagram of a left foot having a monolithic calcaneal prosthesis 800 having an integral intramedullary nail 850 formed of a single piece of material. The calcaneal prosthesis 800 is configured to approximate the shape and function of a natural calcaneus, including the calcaneal tuberosity 819. In some embodiments, the prosthesis 800 has a dorsal surface adapted to abut a resected talus 200 or resected tibia 204. In some embodiments, the prosthesis 800 has an anterior surface adapted to abut a resected cuboid 202 and/or mid-foot bones. In the configuration shown in FIG. 8, the IM nail 850 is configured to be inserted through the talus 200 and the tibia 204, for fusing the calcaneal prosthesis 800, the talus 200 and the tibia 204 together. In other embodiments, for a patient having a severely degraded talus, the prosthesis 800 can have an extended plantar-dorsal height, and the IM nail 850 is configured to extend directly into the tibia 204.

In more detail, as shown in FIGS. 9-12, the calcaneal prosthesis system 880 comprises a body 810 having a dorsal surface 812, a plantar surface 814, a medial surface 813, a lateral surface 815, an anterior surface 816, and a posterior end 818. The anterior (A), medial (M) and dorsal (D) directions are shown in FIG. 8. The posterior end 818 has a tuberosity 819. The tuberosity 819 extends in an oblique direction relative to an anterior-posterior (A) direction of the body.

In some embodiments, the anterior surface 816 has a concavity, convexity or flat surface shaped for receiving the cuboid bone 202 or mid-foot bone(s). For example, the anterior surface 816 can include a concavity 816c as shown in FIG. 8. The concavity is shaped as an articulating surface for articulating motion with respect to the cuboid 202 (or mid-foot bone(s) in a case where the surgeon makes a biplanar wedge cut to the mid-foot). In other embodiments described below with reference to FIGS. 14 and 15, the anterior surface can include a trapezoid-shaped projection or a trapezoid-shaped recess, respectively, for abutting a resected cuboid (not shown) and/or mid-foot bone(s), not shown.

In the example of FIGS. 8-12, the dorsal surface 812 includes a convex surface for engaging a talus bone 200 and/or tibia. For example, because the exemplary prosthesis 800 is intended for use in a fusion surgery, the dorsal surface 812 can include a trapezoid-shaped convexity 830 as shown in FIG. 8, adapted to be received by a recess in a resected talus (not shown). The exemplary trapezoid-shaped convexity 830 has the general form of a truncated pyramid, with trapezoidal surfaces on the medial, lateral, anterior and posterior sides, to facilitate an approach from any direction the surgeon may choose. In other embodiments described below with reference to FIG. 13, the dorsal surface can include a trapezoid-shaped recess, for abutting a corresponding projection of a resected talus (not shown). In other embodiments, a concave or flat surface can be substituted for the convex surface on the dorsal surface 812 of the body. Further, convex surfaces can be curved or can comprise combinations of flat and/or curved surfaces that form a protuberance; concave surfaces can be curved or can comprise combinations of flat and/or curved surfaces that form a recess.

The body 810 and IM nail 850 may be pre-drilled, or pre-made by forging, casting and/or machining. In other embodiments, the body 810 and IM nail 850 are formed as part of an additive manufacturing (AM) process, such as 3D printing or direct metal laser sintering (DMLS) as discussed below. If an AM process is used, the prosthesis 800 is formed as a plurality of stacked monolayers, and the k-wire holes 820 are formed by voids at selected locations within the monolayers. The pre-formed holes 820 may be pre-planned using patient specific planning. For example, the calcaneus prosthesis 800 can be a patient-specific prosthesis designed as a mirror image of a non-degraded calcaneus of the patient's opposite foot. The location and angulation of the implant holes and IM nail hole can be designed using a three-dimensional model to ensure that the fasteners and IM nail do not extend into one or more predetermined sections of a corresponding three-dimensional model of the patient's tissue, as determined by X-ray imagery.

In the case where the prosthesis is molded or formed by additive manufacturing (e.g., 3D printing or direct metal laser sintering), the IM nail 850 is formed at the same time the body 810 is formed. In the case where the prosthesis 800 is formed by machining, the IM nail 850 may be formed at any time point before, during or after machining the body 810. Forming the surface defining hole 804 at the beginning of machining provides more options for stabilizing the piece of material from which the prosthesis is formed during the remainder of the machining. Forming the IM nail 850 during fabrication of the calcaneal prosthesis 800 reduces the length of the surgery preparation and avoids the difficulty of the surgeon drilling an aligned hole in the irregularly shaped calcaneal prosthesis 800.

In some embodiments, the IM nail 850 has a set screw that can be advanced within the nail to compress the joint. Prosthesis 800 can also have additional surfaces defining fixation holes from medial, lateral, or posterior side of the calcaneal prosthesis 800 to fuse calcaneal prosthesis 800 to cuboid and/or mid-foot bones. The fastener opening can be provided at different locations (not shown). The fastener openings can be oriented at a variety of different angles. Additional fastener openings can be included, and the number of fastener openings is not limited to two. For example, some embodiments also have additional surfaces defining fixation holes from medial, lateral, or posterior side of the calcaneal to fuse calcaneal to cuboid and/or mid-foot bones.

The body 810 can have one or more openings 820 for receiving k-wires for external fixation. The example in FIGS. 8-12 has two openings 820, but other embodiments can have any number of openings for external fixation. The openings 820 can extend part way into the body 810 or extend from one (e.g., lateral) side to the opposite (e.g., medial) side as shown. The k-wires can be attached to an external fixation device, such as a circular fixator or the like (not shown).

The IM nail 850 has at least one aperture 851, 852 configured to receive at least one fastener (e.g., a bone screw, not shown).

The IM nail 850 has an elongated shape. In some embodiments, the IM nail has a first diameter D1 along its entire length, as shown in FIG. 8. In other embodiments (as discussed above with reference to FIG. 7, the IM nail has a stop to prevent the IM nail from moving toward the tibia 204 when pressure is applied to the foot.

Although FIGS. 8-12 show a calcaneal prosthesis system 880 for a left foot, a calcaneal prosthesis for the right foot (not shown) can share the same design elements arranged as a mirror image of calcaneal prosthesis system 880 with respect to the mid-sagittal plane.

The single-piece calcaneal prosthesis 800 comprises a unitary (i.e., single-piece, monolithic) body 810 having a dorsal surface 812, a plantar surface 814, an anterior surface 816, and a posterior end 818. The posterior end 818 has a tuberosity 819. The anterior surface 816 can have a concavity 816c shaped for receiving a cuboid bone 202 or mid-foot bone(s). In other embodiments, a convex or flat surface can be substituted for the concavity 816c. The dorsal surface 812 can include a convex surface 830 for engaging a talus bone 200 and/or distal tibia. In other embodiments, a concave or flat surface can be substituted for the convexity 830. The unitary body has an integral IM nail 850 protruding from the dorsal surface 812. In the example of FIG. 8, the integral IM nail protrudes from the convex surface 830 of the dorsal surface 812. In other embodiments, a concave or flat surface can be substituted for the convex surface 830. The integral IM nail 850 has at least one aperture 851, 852 at an end of the IM nail opposite from the body 810. The surgeon can insert fasteners (e.g., bone screws) through the cortical bone of the tibia 204 and/or talus 200 and into the apertures 851, 852 to fix and stabilize the IM nail 850. In some embodiments, the apertures 851, 852 are configured to receive fasteners oriented at an oblique angle relative to a longitudinal axis 840 of the IM nail 850. The body can have one or more openings 820 for receiving k-wires for external fixation.

The single-piece prosthesis 800 can eliminate separate installation steps for the IM nail 850, and eliminate fasteners (e.g., bone screws) for fixing the IM nail 850 to the calcaneal prosthesis. The hole 104 is omitted from the calcaneal prosthesis 800, because the IM nail 850 is not a separate piece and is not inserted into a hole in the calcaneal prosthesis 800. The fastener openings 105, 106 in the side surfaces of the calcaneal prosthesis 100 can also be omitted, because fasteners are not used to lock the IM nail to the calcaneal prosthesis.

The single-piece construction of prosthesis 800 eliminates the separate steps of inserting the calcaneal prosthesis 100 and then inserting the IM nail 150, as described above with reference to FIGS. 1-7. The single-piece prosthesis is implanted from a plantar approach, and thus involves a larger plantar incision than the calcaneal prosthesis system 180. The surgeon makes an incision in the plantar surface of the foot. Any remaining calcaneal bone is removed. The surgeon drills a plantar-dorsal hole through the talus 200 and into the longitudinal axis of the tibia 204. The talus 200 is resected (via lateral or medial approach) to receive the dorsal convexity (or fit into a dorsal concavity) of the calcaneal prosthesis. The prosthesis 800 is inserted nail-first into the wound via plantar approach, and the IM nail 850 is inserted through the talus 200 and into the tibia 204.

Figure 13:
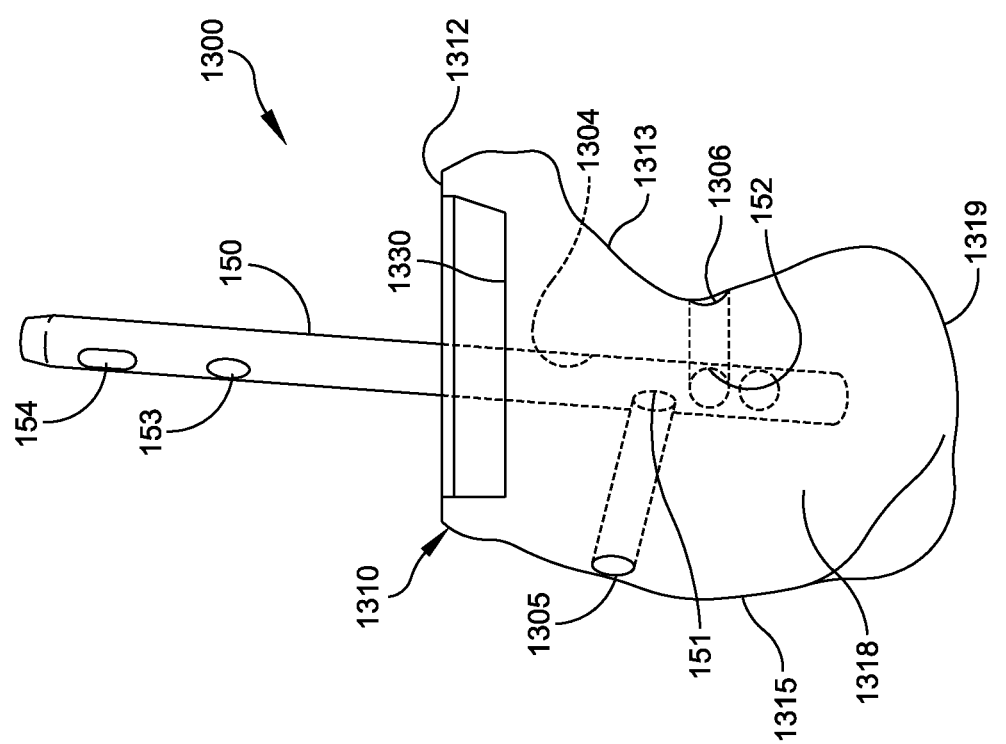
FIG. 13 is a posterior view of a variation of the calcaneal prosthesis system shown in FIG. 3.

FIG. 13 shows a calcaneal prosthesis system 1300 including a calcaneal prosthesis 1310 that is a variation of the calcaneal prosthesis 100. Calcaneal prosthesis 1310 has a dorsal surface 1312, a plantar surface 1314, an anterior surface (not shown), a medial surface 1313, a lateral surface 1315, and a posterior end 1318. The posterior end 1318 has a tuberosity 1319. The anterior surface can have a concavity shaped for receiving the cuboid bone 202 and/or mid-foot bone(s). The calcaneal prosthesis 1310 can be the same as the calcaneal prosthesis 100 except that the anterior surface 1316 of calcaneal prosthesis 1310 has a concave recess 1330 (e.g., a trapezoid-shaped recess) instead of the convexity 130 of calcaneal prosthesis 100. The concave recess 1330 of the calcaneal prosthesis 1310 is configured to receive a resected talus having a trapezoid shaped protuberance. In all other respects, the calcaneal prosthesis 1300 can have the same configuration as the calcaneal prosthesis 100. For brevity, descriptions of the common features of calcaneal prosthesis 1310 and calcaneal prosthesis 100 are not repeated.

Figure 14:
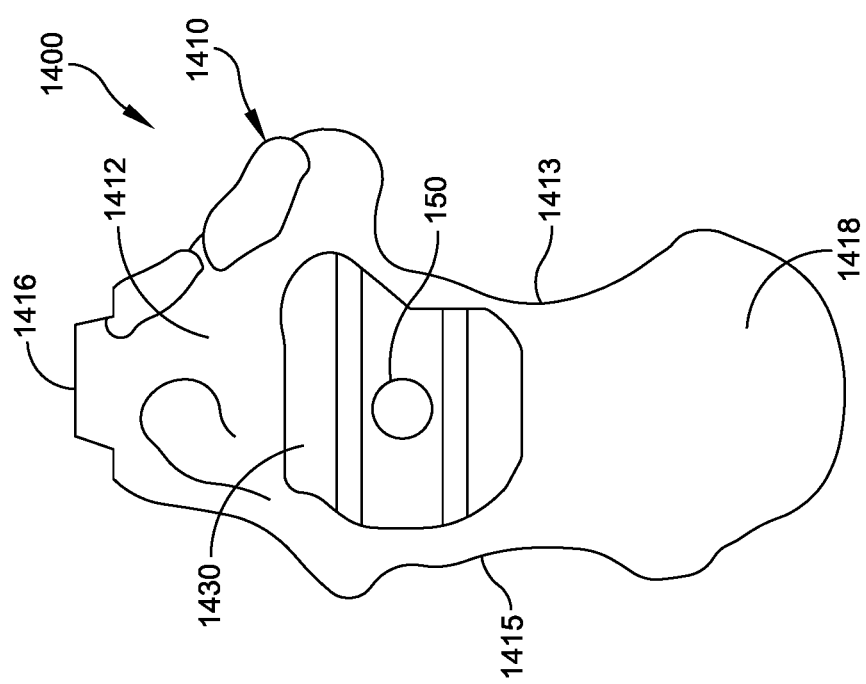
FIG. 14 is a superior view of a variation of the calcaneal prosthesis system of FIG. 1.

FIG. 14 shows a calcaneal prosthesis system 1400 including a calcaneal prosthesis 1410 that is a variation of the calcaneal prosthesis 100. Calcaneal prosthesis 1410 has a dorsal surface 1412, a plantar surface (not shown), a medial surface 1413, a lateral surface 1415, and a posterior end 1418. The posterior end 1418 has a tuberosity (not shown). The calcaneal prosthesis 1410 differs from the calcaneal prosthesis 100 in that the anterior surface 1416 of calcaneal prosthesis 1410 can have a convex protuberance for interfacing to a resected cuboid bone 202 having a trapezoidal recess. The anterior surface 1416 of calcaneal prosthesis 1410 can have a trapezoidal shape. The convex protuberance can provide added stability in the event the surgeon is going to fuse the cuboid 202 to the calcaneal prosthesis 1410. In all other respects, the calcaneal prosthesis 1410 can have the same configuration as the calcaneal prosthesis 100. For brevity, descriptions of the common features of calcaneal prosthesis 1410 and calcaneal prosthesis 100 are not repeated.

Figure 15:
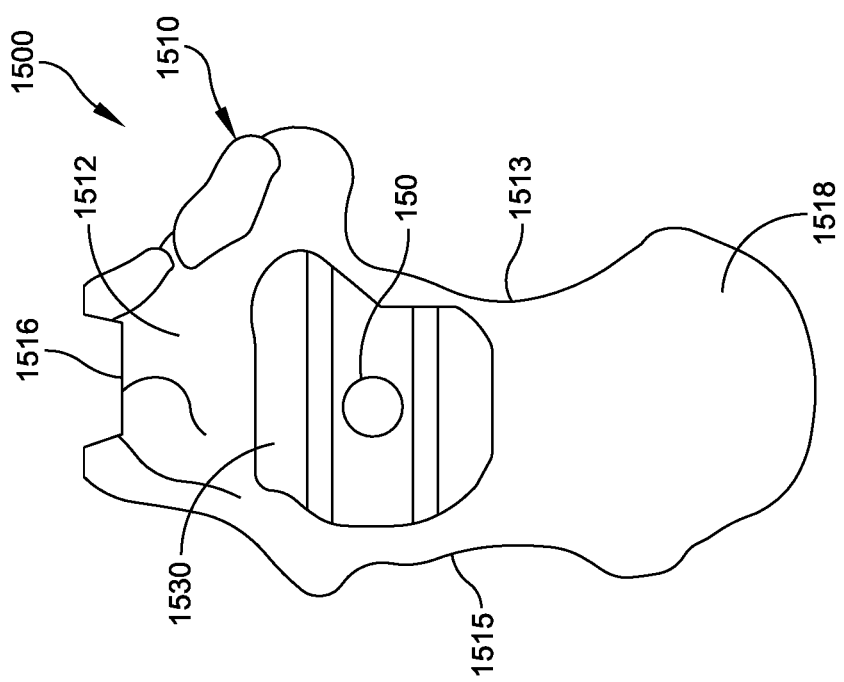
FIG. 15 is a superior view of a variation of the calcaneal prosthesis system of FIG. 14.

FIG. 15 shows a calcaneal prosthesis system 1500 including a calcaneal prosthesis 1510 that is a variation of the calcaneal prosthesis 100. Calcaneal prosthesis 1510 has a dorsal surface 1512, a plantar surface (not shown), a medial surface 1513, a lateral surface 1515, and a posterior end 1518. The posterior end 1518 has a tuberosity (not shown). The calcaneal prosthesis 1510 differs from the calcaneal prosthesis 100 in that the anterior surface 1516 of calcaneal prosthesis 1510 can have a concave recess for interfacing to a resected cuboid bone 202 having a trapezoidal protuberance. The anterior surface 1516 of calcaneal prosthesis 1510 can have a trapezoidal shape. The concave recess can provide added stability in the event the surgeon is going to fuse the cuboid 202 to the calcaneal prosthesis 1510. In some embodiments, the calcaneal prosthesis 1510 has surfaces defining additional holes (not shown) configured to receive fixation screws from through the calcaneal prosthesis and into the cuboid or mid-foot bones. In all other respects, the calcaneal prosthesis 1510 can have the same configuration as the calcaneal prosthesis 100. For brevity, descriptions of the common features of calcaneal prosthesis 1510 and calcaneal prosthesis 100 are not repeated.

Figure 16:
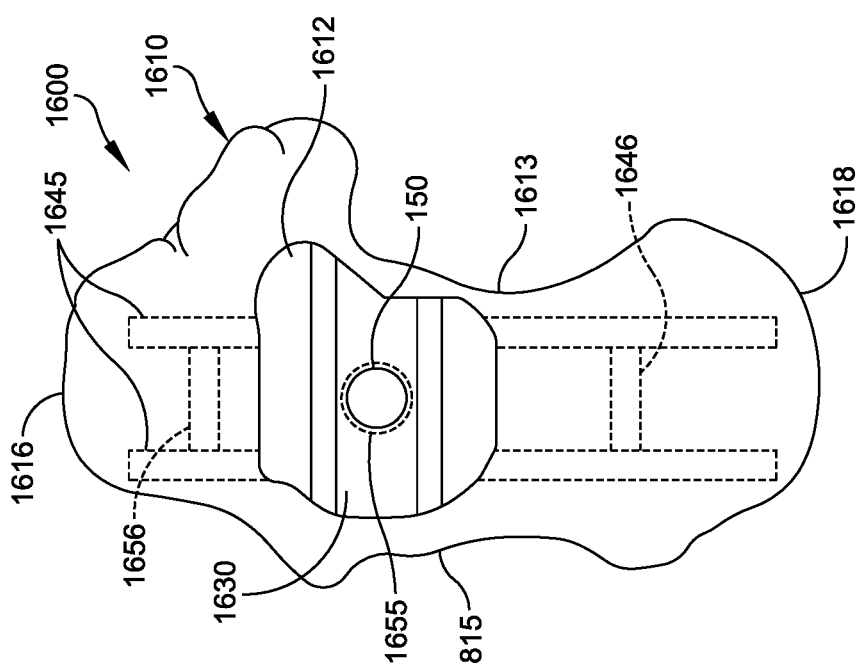
FIG. 16 is a superior view of a variation of the calcaneal prosthesis system of FIG. 1.

FIG. 16 shows a calcaneal prosthesis system 1600 including a calcaneal prosthesis 1610 that is a variation of the calcaneal prosthesis 100. Calcaneal prosthesis 1610 has a dorsal surface 1612, a plantar surface (not shown), a medial surface 1613, a lateral surface 1615, an anterior surface 1616, and a posterior end 1618. The external shape of calcaneal prosthesis 1610 can be the same as the external surface of calcaneal prosthesis 100. For brevity, a description of the external shape of the common features is not repeated. The posterior end 1618 has a tuberosity (not shown). The calcaneal prosthesis 1610 differs from the calcaneal prosthesis 100 in that the internal structure of calcaneal prosthesis 1610 has a lower average density than calcaneal prosthesis 100. Calcaneal prosthesis 1610 can be substantially hollow to reduce weight, and can optionally include struts 1645, 1646 for strength and a tube 1655 extending from the plantar surface (not shown) to the convex portion 1630 of dorsal surface 1612. The struts 1645 and 1646 can be interconnected for additional strength. The tube 1655 is configured to receive the IM nail 150. In all other respects, the calcaneal prosthesis 1610 can have the same configuration as the calcaneal prosthesis 100.

In some embodiments, the calcaneal prosthesis 1610 comprises a porous material throughout the prosthesis. In some embodiments, the interior of the calcaneal prosthesis 1610 has a porous material with a first density and one or more struts 1645, 1646 formed of a continuous solid material having a second density greater than the first density. Other than the struts 1645, 1646, the remainder of the volume of the calcaneal prosthesis 1610 comprises the porous material. The porous material can have the same composition and a lower density than the struts 1645, 1646. A DMLS method can be used to form the calcaneal prosthesis with a variable density.

In the embodiments described above with reference to FIGS. 1-16, the body 110 comprises a biocompatible material from the group consisting of metals such as titanium, stainless steel, absorbable magnesium, metal alloys; polymers such as polyethylene, ultra-high molecular weight polyethylene (UHMWPE), polyether ether ketone (PEEK), Polyetherketone (PEK), absorbable and non-absorbable polymers and copolymers; ceramics such as pyrocarbon; and combinations thereof. stainless steel. Further the body 110 may be coated with materials what may enhance biocompatibility such as, for example, plasma spray, hyaluronic acid, anti-microbial natural and synthetic polymers (e.g., vitamin E).

In the embodiments described above with reference to FIGS. 1-16, the calcaneal prosthesis 100 can be formed by forging, casting, machining or direct metal laser sintering (DMLS). DMLS is an additive manufacturing (AM) process by which products can be printed using a laser or e-beam joining sequential layers of powder metal (e.g., Ti6Al4V or CoCr or Stainless Steel, for example) under automated computer control. Using DMLS, the calcaneal prosthesis 100 can be formed as a highly porous structure. Highly porous structures also provide good bone in-growth properties. Alternatively, the calcaneal prosthesis 100 can be formed as a continuous solid, having a rough surface or a highly porous layer at the surface.

For example, the calcaneal prosthesis 100 can have a porous surface layer with a thickness in a range from 0.01 inch to 0.1 inch. In some embodiments, the porous surface layer has a thickness in a range from 0.03 inch to 0.07 inch. In one example, the porous surface layer has a thickness in a range from 0.04 inch to 0.06 inch. In some embodiments, a first portion of the surface area of the calcaneal prosthesis 100 is porous, and a second portion of the surface area of the calcaneal prosthesis 100 is non-porous. For example, in the embodiment of FIGS. 2-6, the calcaneal prosthesis 100 can have rough surface or porous layer at the dorsal surface 112 of the body 110, and/or at the anterior surface 116 of the body 110, with a smooth surface on the remaining sides. This is a non-exclusive example, and the calcaneal prosthesis can have other combinations of smooth surface(s), rough surface(s) and surfaces having a porous layer.

Figure 17:
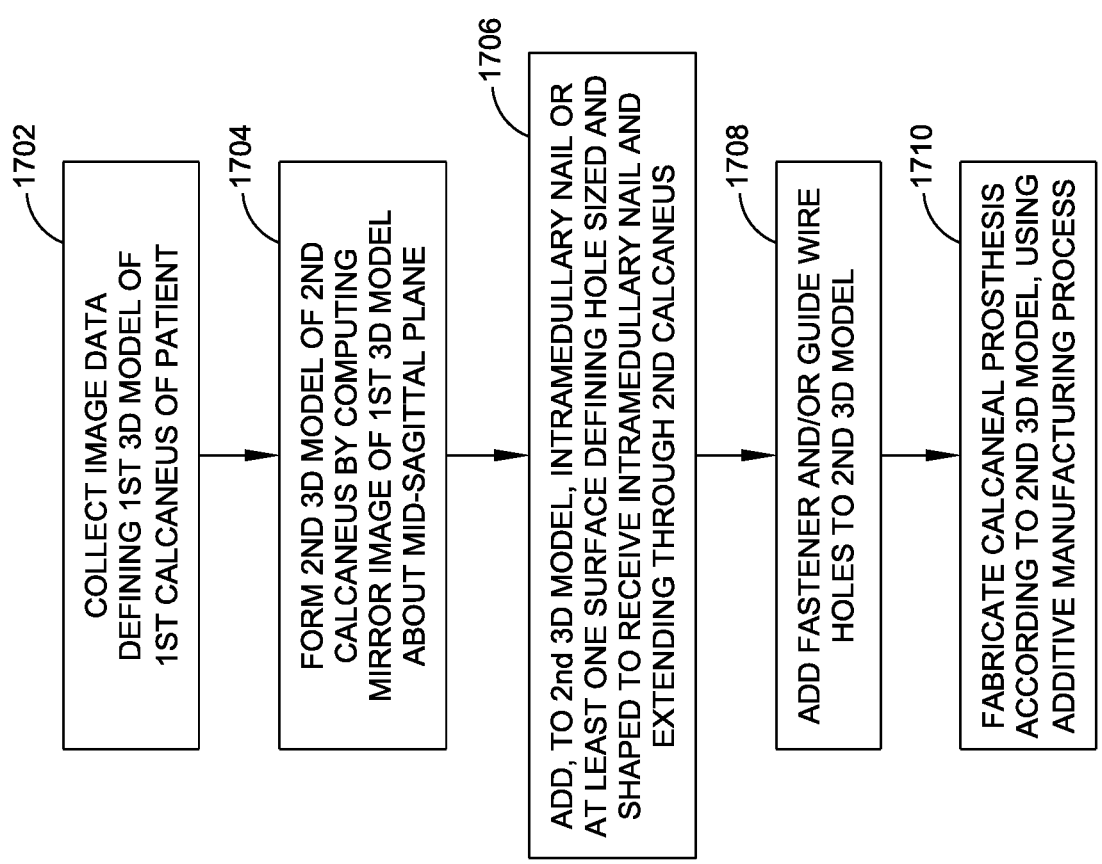
FIG. 17 is a flow chart of a method of making the prosthesis of FIG. 1.

FIG. 17 is a flow chart of a method of making a calcaneal prosthesis as shown in FIGS. 1-16. This method assumes that the patient's feet are symmetrical or nearly-symmetrical about the mid-sagittal plane, except for the deteriorated calcaneus in one foot.

At step 1702, a set of image data are collected to define a first three-dimensional (3D) model of a first calcaneus (the healthy or non-degraded calcaneus) of a patient. The images can be collected by a tomography method, such as X-ray computed tomography (CT) or magnetic resonance imaging (MRI). A series of two-dimensional (2D) images (slices) of the patient's healthy calcaneus are collected. The images also include the talus and tibia. The 3D model is constructed from the 2D images, using a Radon transform, for example.

At step 1704, a second 3D model of a second calcaneus is formed by computing a mirror image of the first 3D model about a sagittal plane.

At step 1706, at least one surface defining a hole is added to the second 3D model. The hole extends through the second calcaneus, and is sized and shaped to receive an intramedullary nail. The hole is positioned so as to lie along the longitudinal axis of the tibia.

At step 1710, fastener holes and/or guide wire holes are added to the 3D model. The location and angulation of the fastener holes and/or guide wire holes are adjusted such that the fasteners, guide wire holes and IM nail do not interfere with each other and do not contact specific tissue portions such as nerves. The location and angulation of the fastener holes, guide wire holes and IM nail hole can be designed using a three-dimensional model to ensure that the fasteners, guide wires (e.g., k-wires) and IM nail do not extend into one or more predetermined sections of a corresponding three-dimensional model of the patient's tissue, as determined by tomography.

At step 1710, the calcaneal prosthesis is fabricated according to the second 3D model, using an additive manufacturing process. For example, the calcaneus prosthesis 100 can be a patient-specific prosthesis designed as a mirror image of a non-degraded calcaneus of the patient's opposite foot.

Although the subject matter has been described in terms of exemplary embodiments, it is not limited thereto. Rather, the appended claims should be construed broadly, to include other variants and embodiments, which may be made by those skilled in the art.

What is claimed is:

1. A calcaneal prosthesis system, comprising:
a body sized and shaped to replace a calcaneus, the body having a dorsal surface, a plantar surface, an anterior surface, and a posterior end,
the posterior end having a tuberosity that approximates a shape of a calcaneal tuberosity,
the anterior surface shaped for engaging at least one of a cuboid bone or a mid-foot bone,
the dorsal surface shaped for engaging at least one of a talus bone or a distal tibia,
the body having a first pre-formed surface defining a hole extending therethrough for receiving an intramedullary (IM) nail, the hole extending from the plantar surface of the body to the dorsal surface.

2. The calcaneal prosthesis system of claim 1, wherein:
the body has a medial surface and a lateral surface, and
the posterior end, the anterior surface, the dorsal surface, the medial surface, or the lateral surface has at least one fastener opening extending to the hole.

3. The calcaneal prosthesis system of claim 2, wherein the at least one fastener opening is oriented at an oblique angle relative to the hole.

4. The calcaneal prosthesis system of claim 2, further comprising an intramedullary (IM) nail shaped to extend through the hole, the IM nail having at least one aperture configured to receive at least one fastener extending through the at least one fastener opening of the body.

5. The calcaneal prosthesis system of claim 4, wherein the IM nail has a first portion with a first diameter and a second portion with a second diameter different from the first diameter, and the surface defining the hole in the body has a first part sized to receive the first portion and a second part sized to receive the second portion.

6. The calcaneal prosthesis system of claim 1, wherein the dorsal surface has a trapezoidal shape.

7. The calcaneal prosthesis system of claim 1, wherein the tuberosity extends in an oblique direction relative to an anterior-posterior direction of the body.

8. The calcaneal prosthesis system of claim 1, wherein the body is patient specific.

9. The calcaneal prosthesis system of claim 8, wherein the dorsal surface of the body is porous.

10. The calcaneal prosthesis system of claim 8, wherein the anterior surface of the body is porous.

11. The calcaneal prosthesis system of claim 1, wherein the body comprises a material having a first density, the body further including one or more struts having a second density greater than the first density.

12. The calcaneal prosthesis system of claim 1, wherein the surface defining the hole limits a depth of insertion of the IM nail.

13. The calcaneal prosthesis of claim 1, wherein the IM nail has at least one aperture at an end of the IM nail opposite from the body.

14. The calcaneal prosthesis of claim 13, wherein the at least one aperture is to configured to receive a fastener oriented at an oblique angle relative to a longitudinal axis of the IM nail.

15. A method of making the calcaneal prosthesis system of claim 1, the method comprising:
  collecting image data defining a first three-dimensional (3D) model of a first calcaneus of a patient;
  forming a second 3D model of a second calcaneus by computing a mirror image of the first 3D model about a sagittal plane; and
  fabricating the body of the calcaneal prosthesis according to the second 3D model, using an additive manufacturing process.

16. The method of making a calcaneal prosthesis according to claim 15, further comprising
  adding to the second 3D model at least one surface defining a first hole that extends through the second calcaneus, the first hole sized and shaped to receive an intramedullary nail; and
  adding at least one fastener hole or guide wire hole to the 3D model, such that the first hole and the fastener hole do not intersect each other.

* * * * *